United States Patent [19]

Fukui et al.

[11] Patent Number: 4,647,412
[45] Date of Patent: Mar. 3, 1987

[54] ANTI-TUMOR DERIVATIVES OF BUTANEDIOL AND PROCESS OF PREPARATION

[75] Inventors: Yoshio Fukui, Osaka; Masatoshi Yamato, Okayama; Naoki Umeda, Osaka; Masahiro Kawasaki, Nara, all of Japan

[73] Assignee: Towa Yakuhin Kabushiki Kaisha, Osaka, Japan

[21] Appl. No.: 683,194

[22] Filed: Dec. 18, 1984

[30] Foreign Application Priority Data

May 24, 1984 [JP] Japan ................. 59-105564

[51] Int. Cl.$^4$ ............... C07C 69/587; C07C 69/533
[52] U.S. Cl. ............................................... 260/410.6
[58] Field of Search ........ 260/410.6, 410.90, 410.9 M; 560/263, 224; 514/546, 549, 552

[56] References Cited

U.S. PATENT DOCUMENTS 3,012,064 12/1961 Hertling et al. .................. 560/263

FOREIGN PATENT DOCUMENTS 577024 6/1959 Canada .......................... 260/410.6
1025238 11/1962 United Kingdom ............ 260/410.6

OTHER PUBLICATIONS

Spartel et al, *Chimie Therapeutique*, 4(3), pp. 207–212, (1969).
Baumann et al, *J. Lipid Res.*, 10, pp. 703–709, (1969).
Langen et al, *Acta Biol. Med. Germ.*, 38(7), pp. 965–974, (1979).
Spartel et al, *Chemical Abstracts*, vol. 71, No. 110174h, (1969).
Langen et al, *Chemical Abstracts*, vol. 92, No. 461a, (1980).
Baumann et al, *Chemical Abstracts*, vol. 72, No. 16639n, (1970).
Ukita et al *Chemical and Pharmaceutical Bulletin*, vol. 9, 1961, pp. 43–46 and 47–53.

*Primary Examiner*—Natalie Trousof
*Assistant Examiner*—Bruce D. Gray
*Attorney, Agent, or Firm*—Wenderoth, Lind & Ponack

[57] ABSTRACT

Provided herein is a butanediol of the formula:

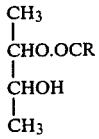

wherein R is an alkyl group containing 5–21 carbon atoms or an alkenyl group containing 5–21 carbon atoms and which contains 1–2 unsaturated bonds. The present invention also contemplates a method of preparing such compounds and the use of such compounds as an anti-tumor agent for treating tumors.

2 Claims, No Drawings

ANTI-TUMOR DERIVATIVES OF BUTANEDIOL AND PROCESS OF PREPARATION

BACKGROUND OF THE INVENTION (a) Field of the Invention

This invention relates to novel derivatives of butanediol represented by the following general formula:

$$\begin{array}{c} CH_3 \\ | \\ CHO.OCR \\ | \\ CHOH \\ | \\ CH_3, \end{array} \quad (I)$$

wherein R is an alkyl group containing 5-21 carbon atoms or an alkenyl group containing 5-21 carbon atoms with 1-2 unsaturated bonds; the preparation of these compounds, and pharmaceutical compositions containing such compounds. The present invention also contemplates a method of preparing such compounds and the use of such compounds as anti-tumor agents.

(b) Description of the Prior Art

With regard to hitherto known anti-tumor agents, undesirous side-effects such as leucopenia, thrombopenia, alopecia, myelosis, nausea, vomiting and diarrhea have been reported after an administration of these agents. There are certain kinds of so-called "folk medicines" which are believed to be effective for treating patients with tumors and such medicines can be administered for a tolerably long period of time without conspicuously undesirous side-effects. For example, it has been reported that the administration of decoctions obtained from the seeds of Chinese pearl barley increased the lifespan of animals suffering from cancer at the terminal stage [M. Nakayama; The Bulletin of The Japan Surgery Association: Vol. 61, pages 234-246 (1960)] and acetone extractions from the seeds of pearl barley had a growth inhibiting activity against the cells of Ehrlich ascites carcinoma in mice and their active component was identified to be butanediol-2,3-cis-9-hexadecenoyl-3-trans-11-octadecenoate [T. Ukita & A. Tanimura: The Chemical & Pharmaceutical Bulletin; Vol. 9, pages 43-46 and 47-53 (1961)]. Further, it was reported that in the investigation for seeking fat-soluble ingredients in the seeds of pearl barley, the existence of coixenolide was not identified when a diester synthesized from 2,3-butanediol and oleyl chloride was employed as a standard substance. [T. Nagao et al: The abstracts from the lectures published at the 103th general meeting of the Japan Pharmaceutical Association (1983, in Tokyo)].

On the basis of above prior art teachings, investigations have been conducted by the present inventors for obtaining butanediol derivatives which will have a strong antitumor activity but have a low toxicity, and this invention has been achieved as a part of our series of investigations.

SUMMARY OF THE INVENTION

This invention relates to novel derivatives of butanediol derivatives of the formula (1) represented by the following formula:

$$\begin{array}{c} CH_3 \\ | \\ CHO.OCR \\ | \\ CHOH \\ | \\ CH_3 \end{array}$$

wherein R is an alkyl group containing 5-21 carbon atoms or an alkenyl group containing 5-21 carbon atoms and in which the alkylene group contains 1-2 unsaturated bonds. The invention also relates to the method of producing such compounds and to pharmaceutical compositions containing such compounds. These compounds and compositions thereof are effective for treating tumors in mammals and are effective to cure or at least inhibit the growth of tumors, sometimes at least causing a state of remission regarding the growth or adverse effects of the malignant tumor thus treated.

Of the compounds represented by the general formula (I), of this invention, as described above, those compounds in which R expresses the residues of the following acids are recommended:

Palmitic acid: $CH_3(CH_2)_{14}.COOH$
Stearic acid: $CH_3(CH_2)_{16}.COOH$
Oleic acid: cis—$CH_3(CH_2)_7CH=CH(CH_2)_7.COOH$
Elaidic acid: trans—$CH_3(CH_2)_7CH=CH(CH_2)_7.COOH$
Erucic acid: $CH_3(CH_2)_7CH=CH(CH_2)_{11}.COOH$
Sorbic acid: $CH_3(CH=CH)_2.COOH$
Linoleic acid: $CH_3(CH_2)_4CH=CH-CH_2-CH=CH(CH_2)_7.COOH$
and geometrical isomers thereof.

DETAILED DESCRIPTION OF THE INVENTION

To prepare the compounds of this invention, a butanediol represented by a formula;

$$\begin{array}{c} CH_3 \\ | \\ CHOH \\ | \\ CHOH \\ | \\ CH_3 \end{array} \quad (II)$$

is dissolved or suspended in inactive solvents such as acetone, diethylether, isopropylether, benzene, toluene, chloroform, ethyl acetate and methylethylketone separately or mixtures thereof, and active derivatives of the compounds represented by a following general formula;

$$R.COOH \quad (III)$$

wherein R is an alkyl group containing 5-21 carbon atoms and an alkenyl group containing 5-21 carbon atoms with 1-2 unsaturated bonds, are added thereto at −20° C. to 20° C., preferably at 4° C. The mixture is then subjected to a reaction in the presence of an active acylating agent. After the reaction, the reactant is stirred for about 1-5 days at 10°-40° C., it is extracted with non-polar sorvents such as diethylether, isopropylether, benzene, chloroform, ethyl acetate, methylethylketone, petroleum ether and cyclohexane and the solvent is distilled off. The thus obtained residue is isolated by a column chromatography and is refined.

EXAMPLES

Example 1

Preparation of 3-hydroxybutane-2-yl-9-cis-octadecenoate

A mixture of 20 g of oleic acid, 16 g of diethylphosphorocyanidate and 6 g of 2,3-butanediol was cooled with ice and 10 ml of triethylamine are added dropwise at a low temperature under stirring for 30 minutes and the mixture was then left for 3 days at room temperature. The reactant was extracted with ethylether and the separated ether layer was washed with 20 ml of potassium bicarbonate, then with 20 ml of water and dried on anhydrous sodium sulfate. After the solvent was distilled off under a reduced pressure, the reactant was refined by a silica gel column chromatography (petroleum ether: ethyl acetate=20:1) and through a fractional distillation under a reduced pressure, a fraction having a boiling point of 160°-180° C./0.05 mmHg was collected.

Example 2

Another preparation of 3-hydroxybutane-2-yl-9-cis-octadecenoate

Into 50 ml of anhydrous benzene, 8.52 g of oleic acid and 2.7 g of 2,3-butanediol were dissolved. Further, 6.18 g of dicyclohexyl carbodiimide and a small quantity of cuprous chloride were added thereto and the mixture was stirred for 3 hours under cooling with ice and was left for 18 hours at room temperature. The reaction mixture was filtered and cyclohexane was added to the filtrate. The separated cyclohexane layer was washed with water and dried on anhydrous sodium sulfate. The solvent was distilled off under a reduced pressure and was refined by a silicagel column chromatography (petroleum ether:ethyl acetate=20:1). The separated effluent was sujected to molecular distillation in sublimation equipment and 3.1 g (Yield: 29%) of viscous oils, which distilled out at 160°-180° C./0.05 mmHg, were collected.

EXAMPLE 3

Preparation of 3-hydroxybutane-2-yl-9-cis-octadecadienoate

Into 50 ml of anhydrous benzene, 8.4 g of linoleic acid and 2.7 g of 2,3-butanediol were dissolved, to which a small quantity of cuprous chloride and 6.18 g of dicyclohexylcarbodiimide were further added. The mixture was stirred for 3 hours under cooling with ice then was left for 18 hours at room temperature and filtered. The filtrate was mixed with ethyl ether to separate the liquids into layers. The separated ether layer was washed with potassium bicarbonate, then with water and dried on anhydrous sodium sulfate. The solvent was removed by distillation and the residue was refined by a silica-gel column chromatography (petroleum ether:ethyl acetate=20:1). The effluent was subjected to molecular distillation by means of sublimation equipment and 6 g (Yield: 57%) of an oily substance, which distilled out at 195°-200° C./0.03 mmHg, was collected.

Compounds other than the ones described above can be obtained in the same manner as described in Examples 1-3.

Of the compounds of this invention which are represented by formula (I):

$$\begin{array}{l} CH_3 \\ | \\ CHO.OCR \\ | \\ CHOH \\ | \\ CH_3, \end{array}$$

wherein R is selected from an alkyl group containing 5-21 carbon atoms and an alkenyl group containing 5-21 carbon atoms with 1-2 unsaturated double bonds, some of the representative compounds will be referred to below:

Compound A (a derivative of sorbic acid)
R: —CH=CH—CH=CH—CH$_3$
   (cis)      (cis)

Compound B (a derivative of palmitic acid)
R: —(CH$_2$)$_{14}$—CH$_3$

Compound C (a derivative of stearic acid)
R: —(CH$_2$)$_{16}$—CH$_3$

Compound D (a derivative of oleic acid)
R: —(CH$_2$)$_7$—CH=CH—(CH$_2$)$_7$—CH$_3$
              (cis)

Compound E (a derivative of elaidic acid)
R: —(CH$_2$)$_7$—CH=CH—(CH$_2$)$_7$—CH$_3$
              (trans)

Compound F (a derivative of linoleic acid)
R: —(CH$_2$)$_7$—CH=CH—CH$_2$—CH=CH—(CH$_2$)$_4$—CH$_3$
              (cis)              (cis)

Compound G (a derivative of erucic acid)
R: —(CH$_2$)$_{11}$—CH=CH—(CH$_2$)$_7$—CH$_3$
                (cis)

Some of the anti-tumor effects, which the representative compounds of this invention exhibit will be demonstrated by the following experiments:

Experiment 1

Comparison of the Compounds of the Present Invention with the Compound 2,3-dioleoyloxybutanediol* in respect to the increase of the life span of test animals treated therewith

*2,3-dioleoyloxybutanediol has the following formula:

$$\begin{array}{l} CH_3 \\ | \\ CHO.OC-(CH_2)_7-CH=CH-(CH_2)_7-CH_3 \\ | \\ CHO.OC-(CH_2)_7-CH=CH-(CH_2)_7-CH_3 \\ | \\ CH_3 \end{array}$$

Groups, each of which consists of 10 ICR male mice of five weeks age, were provided. Into the abdominal cavity of each and every mouse in the group, $10^6$ cells of Ehrlich's ascite carcinoma were inoculated. 24 hours after the inoculation, the compounds of the present invention and the known compound were suspended or dissolved in a 1% physiological saline solution of Tween 80.

Observations were made concerning the capacity of the various compounds to increase the life span of the mice (ILS %). This was calculated by comparing the average span of the mice treated with the various compounds with that of a control group and the increase was designated (ILS %) in the Table I.

TABLE I

| Compound | Dose (mg/Kg of a body weight) | ILS (%) |
|---|---|---|
| 2,3-dioleoyloxy-butanediol | 500 | 22 |
| Compound A | 100 | 29 |
|  | 300 | 22 |
| Compound C | 100 | 1 |
|  | 300 | 9 |
| Compound D | 100 | 37 |
|  | 300 | 56 |
| Compound E | 100 | 43 |
|  | 300 | 64 |
| Compound F | 100 | 28 |
|  | 300 | 63 |
| Compound G | 100 | 66 |
|  | 300 | 65 |

Experiment 2

Test for an increase in the life span of the compounds of the present invention in comparison with oleic acid Groups, each of which consists of 10 ICR male mice of five weeks age, were provided. Into the abdominal cavity of each mouse in the groups, $10^6$ cells of Ehrlich's ascite carcinoma was inoculated. On the next and 7th days after the day of inoculation, solutions of the compounds of the present invention and that of oleic acid were dissolved or suspended separately in a 1% physiological saline solution of Tween 80 and injected into each of the mice. At the same time, a control group was injected with a 1% physiological saline solution of Tween 80.

Observations were made on the capacity of the various compounds to prevent the death of the mice or increase the life span and the capacity of the compounds to increase the life span was made by determining the ratio of the life span of mice treated as compared with those of a control group in which the mice were not treated with medication.

| Compound | Dose (mg/Kg of a body weight) | ILS (%) |
|---|---|---|
| Oleic acid | 300 | 9 |
| Compound C | 300 | 40 |
| Compound D | 300 | 61 |
| Compound E | 300 | 64 |
| Compound F | 300 | 34 |

Experiment 3

Test for comparing the weight of tumors treated with compounds of the present invention as compared with erucic acid Groups, each of which consists of 8 ICR male mice of five weeks of age, were provided. Into the under part of the inguinal canals of every mouse in the groups, $10^7$ cells of Ehrlich's ascite carcinoma were inoculated. On the 3rd and 4th successive days from the day of inoculation, the erucic acid and compounds of the present invention were each dissolved or suspended separately in a 1% physiological saline solution of Tween 80, and injected into the abdominal cavity of every mouse once a day for five days. At the same time, the control group was injected with a 1% physiological saline solution of Tween 80. On the 10th day from the day of inoculation, the tumors produced in the mice by inoculation were removed and weighed.

The ratio of the average weight of the tumors between the groups treated with the aforementioned compounds and that of the control group (T/C %)** is shown below in Table III:

**Note: The symbol for T/C % signifies Control—Treatment/Control %.

TABLE III

| Compound | Dose (mg/Kg of a body weight) | Change of a body weight (g) | T/C % |
|---|---|---|---|
| 1% physiological saline solution of Tween 80 |  | +3.5 |  |
| Erucic acid | 100 | +4.1 | −14 |
|  | 300 | +3.3 | 10 |
|  | 500 | +3.0 | 29 |
| Compound G | 100 | +2.2 | 15 |
|  | 300 | −0.2 | 53 |
|  | 500 | −1.6 | 55 |

Experiment 4

Acute toxicity

Groups, each of which consists of 5 ICR male mice of five weeks old, were used. The compounds of the present invention were suspended in a 1% Tween 80-saline. The suspensions were injected intraperitoneally of each of the mice in the groups and they were observed for two weeks in respect to their condition and life span.

No dead mice were found in the groups in which Compound D, E and G were injected respectively in an amount of 3000 mg per Kg of body weight.

From the results of the above four experiments, it can be understood that the compounds of the present invention exhibit prominent anti-tumor effects, nevertheless, they possess a low toxicity.

The anti-tumor compositions containing the butanediol derivatives of this invention as an active ingredient, may be selected from the group consisting of tablets, capsules, syrups, injections, ointments, etc., and these forms of composition can be prepared by conventional methods known in the pharmaceutical fields. The pharmaceutical preparations of this invention can be administered through an oral or a parenteral route.

The administration dosage of the compounds of the present invention should be about 1–500 mg per kilogram of body weight of the mammal, such as an adult patient and the dosage can be administered 1–6 times a day. This is the basal dose, however, it should be understood that the dosage may be varied depending upon the illness of the patient.

The physical properties of some of the representative compounds of this invention will be listed below:

Compound A

Yield of production: 13%.
Distillation temperature: 110°–120° C./0.04 mmHg.
IR $\nu_{max}^{Neat}$ cm$^{-1}$: 3450 (OH), 1700 (C=O).
$^1$H-NMR (CDCl$_3$) δ: 1.21 (3H, d, J=6 Hz), 1.35 (3H, d, J=6 Hz), 1.87 (3H, d, J=4 Hz), 3.07–3.54 (1H, broad) 3.56–4.18 (1H, m), 4.59–5.27 (1H, m), 5.87 (2H, d, J=16 Hz), 6.08–6.54 (2H, m), 7.08–7.38 (1H, m).
Mass spectrum m/e(M+): 184.

Compound B

Yield of production: 23%.
Distillation temperature: 160°–180° C./0.01 mmHg.

IR $\nu_{max}^{Neat}$cm$^{-1}$: 3450 (OH), 1735 (C=O).
$^1$H-NMR (CDCl$_3$) δ: 0.62–1.07 (3H, m), 1.07–1.85 (32H, m), 2.00–2.53 (2H, m), 2.95–3.45 (1H, broad), 3.65–4.10 (1H, m), 4.65–5.12 (1H, m).
Mass spectrum m/e(M+): 328.

Compound C

Yield of production: 30%.
Melting point: 69°–70° C.
IR $\nu_{max}^{Neat}$cm$^{-1}$: 3350 (OH), 1655 (C=O).
$^1$H-NMR (CDCl$_3$) δ: 0.60–1.00 (3H, m), 1.00–1.86 (30H, m), 1.86–2.55 (3H, m), 3.40–4.11 (1H, m), 4.50–5.11 (1H, m).
Mass spectrum m/e(M+): 356.

Compound D

Yield of production: 29%.
Distillation temperature: 160°–180° C./0.05 mmHg.
IR $\nu_{max}^{Neat}$cm$^{-1}$: 3450 (OH), 1735 (C=O).
$^1$H-NMR (CDCl$_3$) δ: 0.66–1.06 (3H, m), 1.06–1.84 (28H, m), 1.84–2.56 (6H, m), 2.56–3.06 (1H, broad), 3.50–4.08 (1H, m), 4.50–5.01 (1H, m), 5.26–5.61 (2H, t, J=5 Hz).
Mass spectrum m/e(M+): 354.

Compound E

Yield of production: 25%.
Distillation temperature: 140°–150° C./0.03 mmHg.
IR $\nu_{max}^{Neat}$cm$^{-1}$: 3450 (OH), 1735 (C=O), 1715 (C=O).
$^1$H-NMR (CDCl$_3$) δ: 0.48–1.08 (3H, m), 1.08–1.70 (28H, m), 1.70–2.56 (6H, m), 2.84–3.35 (1H, broad), 3.60–4.14 (1H, m), 4.62–5.07 (1H, m), 5.37–5.63 (2H, m).
Mass spectrum m/e(M+): 354.

Compound F

Yield of production: 57%.
Distillation temperature: 195°–200° C./0.03 mmHg.
IR $\nu_{max}^{Neat}$cm$^{-1}$: 3370 (OH), 1735 (C=O).
$^1$H-NMR (CDCl$_3$) δ: 0.67–1.08 (3H, m), 1.08–1.86 (22H, m), 1.86–2.57 (7H, m), 2.57–2.97 (2H, m), 3.47–4.06 (1H, m), 4.52–5.08 (1H, m), 5.20–5.62 (4H, m).
Mass spectrum m/e(M+): 352.

Compound G

Yield of production: 11%.
Distillation temperature: 155° C./0.07 mmHg.
IR $\nu_{max}^{Neat}$cm$^{-1}$: 3450 (OH), 1735 (C=O).
$^1$H-NMR (CDCl$_3$) δ: 0.70–1.10 (3H, m), 1.10–1.83 (36H, m), 1.84–2.55 (6H, m), 2.84–3.35 (1H, broad), 3.50–4.05 (1H, m), 4.55–5.05 (1H, m), 5.37 (2H, t, J=5 Hz).
Mass spectrum m/e(M+): 410.

What we claim is:
1. A butanediol derivative which is 3-linoleoyloxy-2-butanol.
2. A butanediol derivative which is 3-erucoyloxy-2-butanol.

* * * * *